United States Patent [19]

Diehr et al.

[11] Patent Number: 4,910,316

[45] Date of Patent: Mar. 20, 1990

[54] PROCESS FOR PREPARING 2,4-DICHLORO-5-DICHLOROMETHYL-THIAZOLE

[75] Inventors: Hans-Joachim Diehr, Wuppertal; Gunther Beck, Leverkusen, both of Fed. Rep. of Germany

[73] Assignee: Bayer Aktiengesellschaft, Leverkusen, Fed. Rep. of Germany

[21] Appl. No.: 244,226

[22] Filed: Sep. 14, 1988

[30] Foreign Application Priority Data

Sep. 22, 1987 [DE] Fed. Rep. of Germany ....... 3731803

[51] Int. Cl.$^4$ ............................................ C07D 277/20
[52] U.S. Cl. .................................................... 548/202
[58] Field of Search ........................................ 548/202

[56] References Cited

FOREIGN PATENT DOCUMENTS

| 0192148 | 8/1986 | European Pat. Off. ............ 548/202 |
| 2525442 | 12/1976 | Fed. Rep. of Germany ...... 548/202 |
| 3303704 | 8/1984 | Fed. Rep. of Germany ...... 548/202 |
| 3505900 | 8/1986 | Fed. Rep. of Germany ...... 548/202 |
| 3505902 | 8/1986 | Fed. Rep. of Germany ...... 548/202 |
| 62-48642 | 3/1987 | Japan ................................. 548/202 |

OTHER PUBLICATIONS

Potts, Comprehensive Heterocyclic Chemistry, vol. 6, p. 280 (1984).
Melvin S. Newman et al, "Conversion of Aromatic and α,β-Unsaturated Aldehydes . . . ", J. Org. Chem., vol. 43 (1978), pp. 4367–4368.
Arthur J. Hill et al, "Studies on the Preparation of the Higher Acetylenes . . . ", J. Am. Chem. Soc., 50 (1928), pp. 172–177.

*Primary Examiner*—Robert Gerstl
*Attorney, Agent, or Firm*—Sprung, Horn, Kramer & Woods

[57] ABSTRACT

A process for preparing 2,4-dichloro-5-dichloromethyl-thiazole of the formula

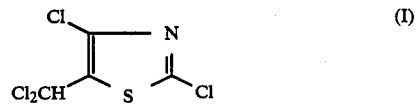

which comprises reacting 2,4-dichloro-5-thiazole-carboxaldehyde of the formula

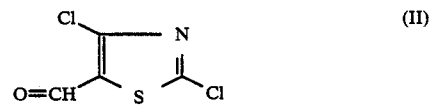

with thionyl chloride (SOCl$_2$) in the presence of a halogenating catalyst at a temperature between 0° C. and 100° C. Preferred catalysts are aprotic organic nitrogen or phosphorus compounds. The products are directly obtained in high yield and purity so they can be directly used as bactericides or as intermediates for herbicides.

5 Claims, No Drawings

PROCESS FOR PREPARING 2,4-DICHLORO-5-DICHLOROMETHYL-THIAZOLE

The invention relates to a novel process for preparing 2,4-dichloro-5-dichloromethyl-thiazole.

It is already known that 2,4-dichloro-5-dichloromethyl-thiazole is obtained by reacting 2,4-dichloro-5-methyl-thiazole with chlorine at elevated temperature upon irradiation with light (cf. DE-OS (German Published Specification) 3,505,900 and DE-OS (German Published Specification) 3,505,902). However, this reaction always gives mixtures of products which contain substantial quantities of 2,4-dichloro-5-trichloromethyl-thiazole in addition of 2,4-dichloro-5-dichloromethyl-thiazole.

It is further known that certain aliphatic or aromatic aldehydes such as, for example, 1-heptanal or benzaldehyde can be converted into the corresponding dichloromethyl compounds by reacting them with phosphorus pentachloride or with thionyl chloride (cf. J. Am. Chem. Soc. 50 (1928), 172–177; J. Org. Chem. 43 (1978), 4367–4369; DE-OS (German Published Specification) 2,525,442). However, the preparation of heterocyclic dichloromethyl compounds from heterocyclic aldehydes has to date not been reported.

It has now been found that 2,4-dichloro-5-dichloromethyl-thiazole of the formula (I)

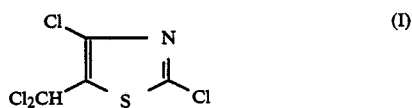

is obtained by reacting 2,4-dichloro-5-thiazole-carboxaldehyde of the formula (II)

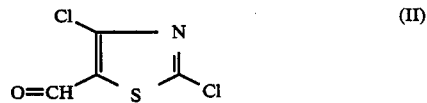

with thionyl chloride (SOCl₂) in the presence of a halogenating catalyst at temperatures between 0° C. and 100° C.

Surprisingly, 2,4-dichloro-5-dichloromethyl-thiazole can be obtained by the process according to the invention in significantly higher yield than by the previously known preparative process.

Advantages of the novel process reside in the fact that it can be carried out in a simple manner and that it provides the product of the formula (I) in such high purity that a purification by distillation is unnecessary.

The reaction sequence of the process according to the invention can be outlined by the following formula scheme:

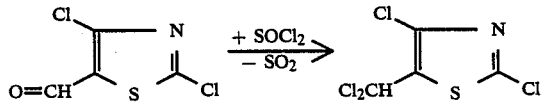

The 2,4-dichloro-5-thiazole-carboxaldehyde of the formula (II) to be used as the starting material in the process according to the invention is already known (cf. DE-OS (German Published Specification) 3,303,704).

The process according to the invention is carried out in the presence of a halogenating catalyst. These catalysts are to be understood to mean compounds which are usually used as catalysts in reactions in which organically bound oxygen is replaced by halogen. Preferred halogenating catalysts are as follows:

(a) aprotic organic nitrogen compounds such as, for example, trimethylamine, triethylamine, tripropylamine, tributylamine, N,N-dimethylaniline, N,N-diethylaniline, N,N-dimethyl-benzylamine, N,N,-diethylbenzylamine, N,N-dimethyl-cyclohexylamine, pyridine, 2-methyl-, 2-ethyl-, 3-methyl-, 3-ethyl-, 4-methyl- and 4-ethyl-pyridine, 2,4-dimethyl- and 2,6-dimethyl-pyridine, 2,4,6-trimethylpyridine, 5-ethyl-2-methyl-pyridine, 1,5-diazabicyclo[4,3,0]-5-nonene (DBN), 1,8-diazabicyclo-[5,4,0]-7-undecene (DBU), 1,4-diazabicyclo-[2,2,2]-octane (DABCO), dimethylformamide, diethylformamide, dipropylformamide, dibutylformamide and dimethylacetamide, (b) aprotic organic phosphorus compounds, such as, for example, tributylphosphine, triphenylphosphine, triscyanoethylphosphine, triphenylphosphine dichloride, tributylphosphine oxide, triphenylphosphine oxide and 1-methyl-1-oxo-phospholine.

Halogenating catalysts which are particularly preferably used for the process according to the invention are triethylamine, tripropylamine, tributylamine, N,N-dimethylbenzylamine, 1-methyl-1-oxo-phospholine and pyridine.

The reaction temperatures for the process according to the invention can be varied within a broad range. In general, the reaction is carried out at temperatures between 0° C. and 100° C., preferably at temperatures between 20° C. and 95° C.

The process according to the invention is generally carried out at atmospheric pressure. However, it is also possible to conduct it under increased or reduced pressure.

The process according to the invention is carried out by using in general 1 to 10 mols, preferably 2 to 5 mols, of thionyl chloride and 0.005 to 0.5 mol, preferably 0.01 to 0.1 mol, of a halogenating catalyst per mol of 2,4-dichloro-5-thiazole-carboxaldehyde of the formula (II).

For the reaction, the reaction components can be mixed in any desired sequence.

In a preferred embodiment of the process according to the invention, thionyl chloride and the halogenating catalyst are initially introduced, and the aldehyde of the formula (II) is slowly metered in. The entire reaction mixture is heated at 30° C. to 50° C. for 1 to 2 hours and then heated at 80° C. to 95° C. until no significant evolution of gas can be observed any longer.

The work-up can be carried out by conventional methods. Preferably, excess thionyl chloride is distilled off, and the residue is stirred or shaken with water and an organic solvent which is virtually nonmiscible with water such as, for example, cyclohexane. The organic layer is separated off, washed with water, and the solvent is distilled off. The remaining residue essentially contains the product of the formula (I), which in general does not have to be further purified.

The 2,4-dichloro-5-dichloromethyl-thiazole of the formula (I) to be prepared by the process according to the invention can be used as a bactericide in plant protection or as an intermediate for preparing herbicides (cf. DE-OS (German Published Specification) 3,505,900).

PREPARATION EXAMPLES

Example 1

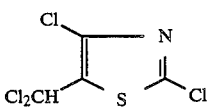

18.2 g (0.1 mol) of 2,4-dichloro-5-thiazolecarboxaldehyde are slowly added to a mixture of 35.7 g (0.3 mol) of thionyl chloride and 0.5 ml of triethylamine at 20° C. The reaction mixture is initially stirred at 40° C. to 45° C. for one hour and then heated at 90° C. to 95° C. for 3 hours. Excess thionyl chloride is distilled off, and 100 ml each of water and cyclohexane are added to the remaining oil. The organic layer which is separated off is washed with 50 ml of water, and the organic solvent is then carefully distilled off.

This gives 2,4-dichloro-5-dichloromethyl-thiazole as an oily residue. Yield: 24.6 g (98% of theory—having a content of 94.7% determined by gas chromatography).

The following table shows the results of reactions carried out analogously with different halogenation catalysts.

TABLE

Results of additional reactions

| Example No. | Halogenation catalyst (amount used) | Yield (% of theory) |
|---|---|---|
| 2 | dimethylformamide (0.5 ml) | 85 |
| 3 | pyridine (0.5 ml) | 99 |
| 4 | 4-dimethylamino-pyridine (0.5 g) | 84 |
| 5 | 1,8-diazabicyclo-[5,4,0]-7-undecene (0.5 ml) | 82 |
| 6 | triphenylphosphine oxide (1 g) | 79 |
| 7 | tri-n-butylamine (0.5 ml) | 84 |
| 8 | N,N—dimethyl-benzylamine (0.5 ml) | 95 |
| 9 | 1-methyl-1-oxo-phospholine (0.5 ml) | 96 |

It will be appreciated that the instant specification and claims are set forth by way of illustration and not limitation, and that various modifications and changes may be made without departing from the spirit and scope of the present invention.

What is claimed is:

1. A process for preparing 2,4-dichloro-5-dichloromethylthiazole of the formula

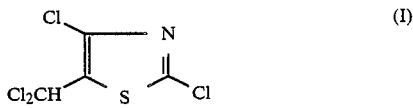

which comprises reacting 2,4-dichloro-5-thiazole-carboxaldehyde of the formula

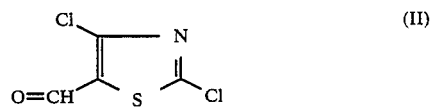

with thionyl chloride ($SOCl_2$) in the presence of an aprotic organic nitrogen compound as a halogenating catalyst at a temperature between 0° C. and 100° C., the catalyst being selected from the group consisting of trimethylamine, triethylamine, tripropylamine, N,N-dimethylaniline, N,N-diethylaniline, N,N-dimethyl-benzylamine, N,N-diethyl-benzylamine, N,N-dimethyl-cyclohexylamine, pyridine, 2-methyl-pyridine, 2-ethyl-pyridine, 3-methyl-pyridine, 3-ethyl-pyridine, 4-methyl-pyridine, 4-ethyl-pyridine, 2,4-dimethyl-pyridine, 2,6-dimethyl-pyridine, 5-ethyl-2-methyl-pyridine, 2,4,6-trimethyl-pyridine and 1,4-diazabicyclo-[2,2,2]-octane (DABCO).

2. A process according to claim 1, wherein the reaction is carried out at a temperature between 20° C. and 95° C.

3. A process according to claim 1, wherein about 1–10 mols of thionyl chloride ($SOCl_2$) and 0.005–0.5 mol of a halogenating catalyst are used per mol of 2,4-dichloro-5-thiazolecarboxaldehyde.

4. A process according to claim 1, wherein about 2–5 mols of thionyl chloride and 0.01–0.1 mol of a halogenating catalyst are used per mol of 2,4-dichloro-5-thiazolecarboxaldehyde.

5. A process according to claim 1, wherein the catalyst is triethylamine, tripropylamine, N,N-dimethylbenzylamine or pyridine.

* * * * *